United States Patent [19]

Spinelli

[11] Patent Number: 5,235,976
[45] Date of Patent: Aug. 17, 1993

[54] METHOD AND APPARATUS FOR MANAGING AND MONITORING CARDIAC RHYTHM USING ACTIVE TIME AS THE CONTROLLING PARAMETER

[75] Inventor: Julio C. Spinelli, Shoreview, Minn.

[73] Assignee: Cardiac Pacemakers, Inc., St. Paul, Minn.

[21] Appl. No.: 806,626

[22] Filed: Dec. 13, 1991

[51] Int. Cl.⁵ .................................................. A61N 1/39
[52] U.S. Cl. ............................................................ 607/25
[58] Field of Search ........................ 128/419 D, 419 PG

[56] References Cited

U.S. PATENT DOCUMENTS

| | | |
|---|---|---|
| 3,593,718 | 7/1971 | Krasner . |
| 4,009,721 | 3/1977 | Alcidi . |
| 4,114,628 | 9/1978 | Rizk .................. 128/419 D |
| 4,140,132 | 2/1979 | Dahl . |
| 4,228,803 | 10/1980 | Rickards . |
| 4,291,699 | 9/1981 | Geddes et al. ............... 128/419 D |
| 4,399,820 | 8/1983 | Wirtzfeld et al. . |
| 4,543,954 | 10/1985 | Cook et al. . |
| 4,686,987 | 8/1987 | Salo et al. ............... 128/419 PG |
| 4,708,143 | 11/1987 | Schroeppel ............... 128/419 PG |
| 4,733,667 | 3/1988 | Olive et al. ............... 128/419 PG |
| 4,773,401 | 9/1988 | Citak et al. ............... 128/419 PG |
| 4,856,522 | 8/1989 | Hansen ................... 128/419 PG |
| 4,895,151 | 1/1990 | Grevis et al. ................. 128/419 D |
| 4,899,752 | 2/1990 | Cohen . |
| 4,925,443 | 5/1990 | Heilman et al. .............. 128/419 PG |
| 5,003,975 | 4/1991 | Hafelfinger et al. ........ 128/419 PG |
| 5,025,784 | 6/1991 | Shao et al. ................ 128/419 PG |
| 5,109,842 | 5/1992 | Adinolfi ..................... 128/419 D |

Primary Examiner—William E. Kamm
Attorney, Agent, or Firm—Haugen and Nikolai

[57] ABSTRACT

A cardiac rhythm management device is described in which the rate controlling parameter of a rate adaptive pacemaker is the heart's total active time. The active time is evaluated using the intraventricular impedance technique, the active time being the length of the interval between the onset of contraction and the point where a line passing through two points on the fast filling segment of the impedance wave form reaches the impedance level corresponding to the end-diastole impedance of the preceding beat. The approach results in a upper rate limit corresponding to the maximum heart rate that does not compromise circulatory function, e.g., result in a decrease in cardiac output, or an increase in cardiac workload without an associated increase in cardiac output. The application also teaches the use of the heart's total active time as an indication of hemodynamic instability for triggering a defibrillation.

10 Claims, 2 Drawing Sheets

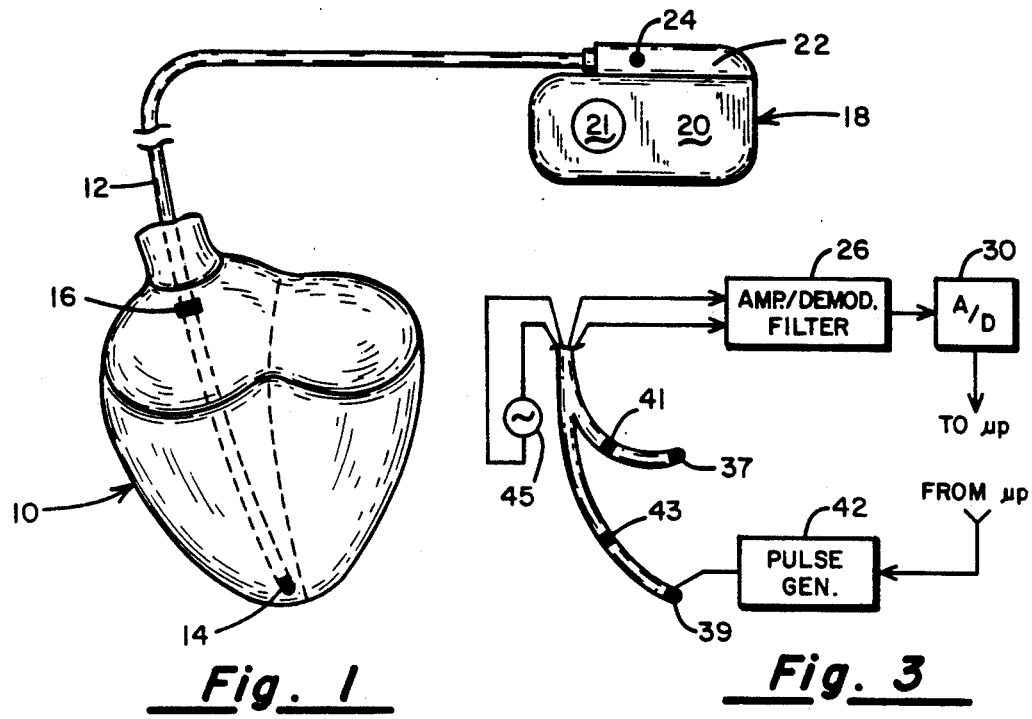
Fig. 1
Fig. 3
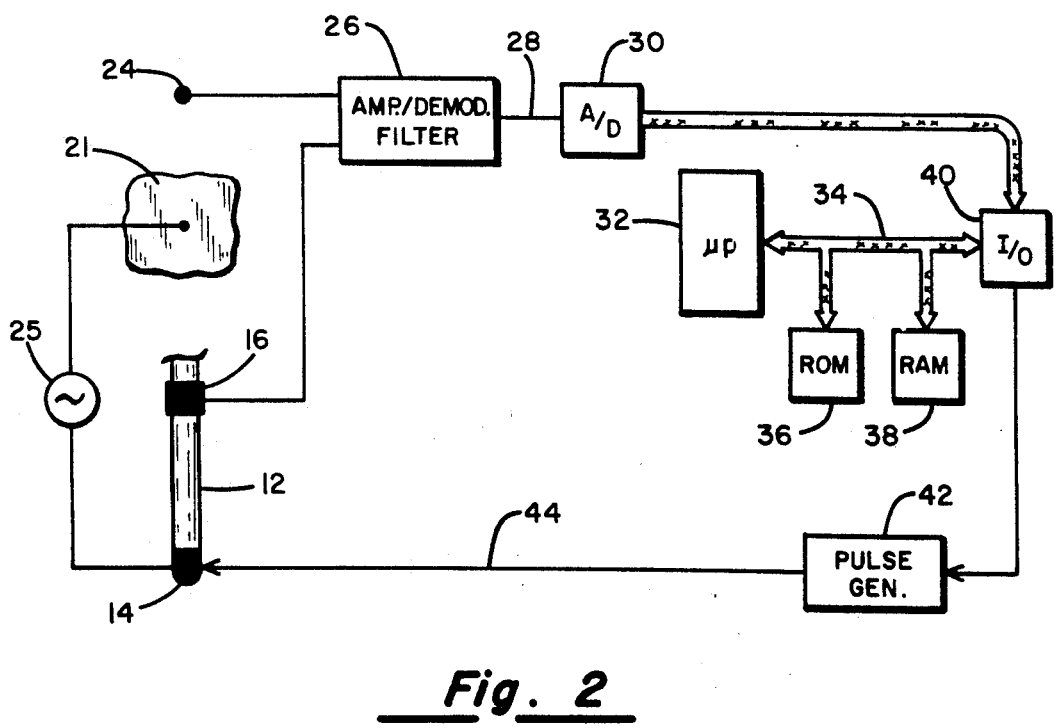
Fig. 2

METHOD AND APPARATUS FOR MANAGING AND MONITORING CARDIAC RHYTHM USING ACTIVE TIME AS THE CONTROLLING PARAMETER

BACKGROUND OF THE INVENTION

I. Field of the Invention

This invention relates generally to cardiac rhythm management devices including bradycardia pacemakers, cardioverters and defibrillators, and more particularly to a device in which the heart's Active Time is used as a controlling variable.

II. Discussion of the Prior Art

Beginning in about 1976, a variety of cardiac pacemakers have been developed and disclosed in which a physiologic or a non-physiologic sensor is used to produce a signal which is intended to be proportional to the level of work or exercise being performed by the patient. Specifically, in 1977, Dr. Mario Alcidi, in U.S. Pat. No. 4,009,721, described a system in which blood pH is sensed and a control signal proportional thereto is developed for altering the rate of an implanted pacemaker. That device has not proven to be commercially successful because it is difficult to implement. Stable pH electrodes are not generally available. The measurement is not related directly to exercise level and any feedback of information as to hemodynamic instability is too slow.

The Cook et al. U.S. Pat. No. 4,543,954 describes a system in which blood temperature becomes the rate controlling parameter for an implanted pacemaker. While blood temperature is found to increase during exercise and emotional stress, the main problems in using temperature as a rate controlling parameter are that the response to the onset of exercise is too slow and temperature change is found not to be proportional to the exercise level. Again, no hemodynamic feedback information is provided when this approach is utilized.

The Richards U.S. Pat. No. 4,228,803 disclose the idea of using the QT interval of the electrocardiogram as the rate control parameter. This interval is found to decrease with increases in exercise. While it has been shown useful for some patients, the technique suffers from the problem that the T-wave is difficult to sense and the interval itself changes between sensed and paced beats, providing only relative values. Beta blockage results in inhibition of catecholamine response and therefore reduction of the stimulus-to-T-wave change. The approach also does not provide any hemodynamic feedback relating to the effect of the heart rate change on the circulatory system.

Still another variety of rate adaptive pacemaker incorporates a pressure sensor for detecting blood pressure changes. See U.S. Pat. No. 4,899,752 to Cohen. Such a sensor is used to measure the rate of increase of the intraventricular pressure. Increased pressure gradient is associated with cardiovascular stress through increased circulating catecholamines and the Frank-Starling response. The Frank-Starling law provides that as increases in venous return further distends the ventricle, the myocardiofibers contract with greater force. Circulating catecholamines, such as epinephrine, cause increased contractile force by affecting beta receptors. This increase in the rate of pressure rise is sensed by a pressure transducer in a pacing lead capable of measuring pressure changes. The rate of change in pressure is changed by the dynamics of the contraction. Therefore, intrinsic and paced beats result in different level signals leading to rate changes which are not exercise-related.

The Wirtzfeld U.S. Pat. No. 4,399,820 employs a sensor capable of measuring oxygen saturation of venous blood for developing a rate control signal as a function thereof. Because oxygen saturation of venous blood decreases with increased exercise, low work loads cause a significant decrease in oxygen saturation. Changes are not linearly related to the applied load. Moreover, leads for monitoring oxygen saturation tend to be quite complex and are not $ particularly reliable over a long term. The device does not provide hemodynamic feedback.

The Dahl U.S. Pat. No. 4,140,132, assigned to Medtronics, Inc., describes a rate adaptive pacer which is perhaps the most widely used rate adaptive system. It relies upon motion or activity, but there is a lack of correlation between motion and the actual work load being experienced by the patient. Thus, its popularity is based principally upon its intrinsic simplicity and not its physiologic response.

In the Krasner U.S. Pat. No. 3,593,718, a lead system is provided for measuring impedance changes in the thoracic cavity. When respiration increases, heart rate generally increases, except for periods of voluntary control of respiration, such as during speech. Both impedance respiratory frequency and impedance respiratory tidal volume are parameters that are sensed. This system does not take into account the change in the artery-venous difference of oxygen concentration that increases the oxygen uptake per liter of inspired air. Oxygen uptake also is susceptible to changes in the oxygen concentration of the inspired gas. This approach does not produce any hemodynamic feedback information to the implanted pacemaker.

The foregoing prior art systems with their mentioned sensors are deficient in that they are incapable of providing the patient an adequate heart rate under all conditions because none is looking at the basic hemodynamics of the heart contraction. An optimized pacing system should be capable of determining the optimum heart rate for the patient under all conditions. While nearly all of the prior art systems alluded to above involve sensors whose outputs are monitored to identify features known to occur during exercise, practically no attention has been focused on monitoring hemodynamic parameters that are crucial to circulatory physiology. For instance, it is commonly assumed that an increase in heart rate will produce an increase in cardiac output. This is not always true. The supposition is correct only if the following two conditions are met:

(1) The heart muscle must be in condition to support the increased work load (calcium availability, lack of ischemia, etc.); and
(2) Sufficient blood must be returning to the heart to maintain cardiac output.

In a healthy individual, exercise increases circulating catecholamine, reduces the pre-ejection interval, increases dP/dT max, decreases the ejection time, and decreases −dP/dT max. All of the above changes decrease the time the ventricle is active, i.e., from the pacing spike to the end of the fast filling phase. The changes with exercise are also associated with an increase in heart rate, which, in turn, decreases passive time, i.e., the diastolic phase. At maximum load, the passive time is very small, with only the fast filling phase in evidence. The maximum heart rate is primarily determined by the capacity of the heart to reduce its total Active Time, and the capacity of the venous system to refill the right and left ventricles during the fast filling phase. As used herein, the term "Active Time" (sometimes abbreviated to "AT") comprises the total time that would elapse from the ventricular pacing pulse or the ventricular sensed R-wave to the end of the filling phase, provided that the ventricles are refilled at the fast filling rate.

OBJECTS

It is accordingly a principal object of the present invention to provide a cardiac rhythm management device in which the heart's Active Time is the controlling parameter in the case of rate adaptive bradycardia pacer antitachypacers or defibrillators.

Another object of the invention is to provide a rate adaptive cardiac pacemaker with means incorporated therein for providing feedback information about the effect of the change in heart rate on the circulatory system such that the heart can be paced at an upper rate limit which does not compromise circulatory function.

Yet another object of the invention is to provide a rate adaptive cardiac pacemaker in which the heart's AT is measured and the length of that time interval is used in developing a rate control signal for varying the escape interval of the pacemaker. In that AT provides a continuously varying measure of the minimum time needed for the heart to refill, it is responsive to changes in venous return and sympathetic and parasympathetic tone.

Still another object of the invention is to provide a rate adaptive cardiac pacemaker whose rate controlling parameter may readily be sensed and which precludes the pacemaker from operating at pacing rates higher than what is needed to assure a minimum filling time.

A still further object of the invention is to provide a cardiac rhythm management device wherein the heart's Active Time is sensed to assess pathologic vs. physiologic tachyrhythmias.

SUMMARY OF THE INVENTION

The foregoing and other objects and advantages of the invention are achieved by providing, as one embodiment, a cardiac pacer with a variable rate pulse generator operative to generate cardiac stimulating pulses in the absence of intrinsic cardiac activity and a means for coupling the pulse generator to the heart for sensing such intrinsic cardiac activity and for applying the stimulating pulses to the heart. The pacer of this invention also includes a means for measuring the total Active Time of the cardiac cycle where the total Active Time is the total time elapsing between the ventricular pacing pulse or the sensed R-wave and the end of the filling phase of the ventricles when the ventricles are being filled at their "fast-filling rate". The measured total AT is then processed in accordance with an algorithm for producing a control signal which is proportional to the measured value. This control signal is then applied to the variable rate pulse generator for controlling the rate at which the cardiac stimulating pulses are produced or for establishing a hemodynamically determined upper rate limit for such a rate adaptive pacer.

The total active time parameter value can be determined by utilizing the impedance versus time signal obtained utilizing the known impedance plethysmography technique disclosed in the Salo et al. U.S. Pat. No. 4,686,987 by extrapolating a line extending through two points in the fast-filling phase of the impedance curve to the point where that line reaches the minimum impedance level determined in the same beat. The total AT is then the interval starting with a natural or paced beat and ending with the point where that linear regression line reaches the end-diastolic impedance from the previous beat.

Hemodynamic stability is maintained by insuring that a stimulating pulse does not occur during the patient's Active Time. It should be clear that if insufficient time is allowed for the heart to fill at the maximum filling rate, i.e., pacing during the fast-filling phase, cardiac output cannot be sustained.

Similarly, AT can be used in an antitachypacer or defibrillator to compare the AT at which the heart was working before the tachyrhythmia is detected and the R-to-R interval of this arrhythmia. If this interval is below a certain percentages of AT, the arrhythmia can be characterized as a hemodynamically unstable, and adequate therapy can be initiated by the device. If a gradual R-R decrease is accompanied by a gradual AT decrease, the resulting high rate can be established as being physiologic (exercise, stress, etc.) and not as a pathologic tachyrhythmia. As such, the use of AT will help the device recognize the source of the rate increase and their hemodynamic consequences.

DESCRIPTION OF THE DRAWINGS

Other features and advantages of the invention will become apparent to those skilled in the art from the following detailed description of a preferred embodiment, especially when considered in conjunction with the accompanying drawings in which:

FIG. 1 is a schematic diagram showing the apparatus used in practicing the present invention;

FIG. 2 is a block diagram of the electronic circuitry helpful in understanding the operation of the apparatus of FIG. 1; and FIG. 3 shows an alternative, two-lead, four-electrode approach for carrying out impedance plethysmography for determining Active Time.

DESCRIPTION OF THE PREFERRED EMBODIMENT

Figure 4:
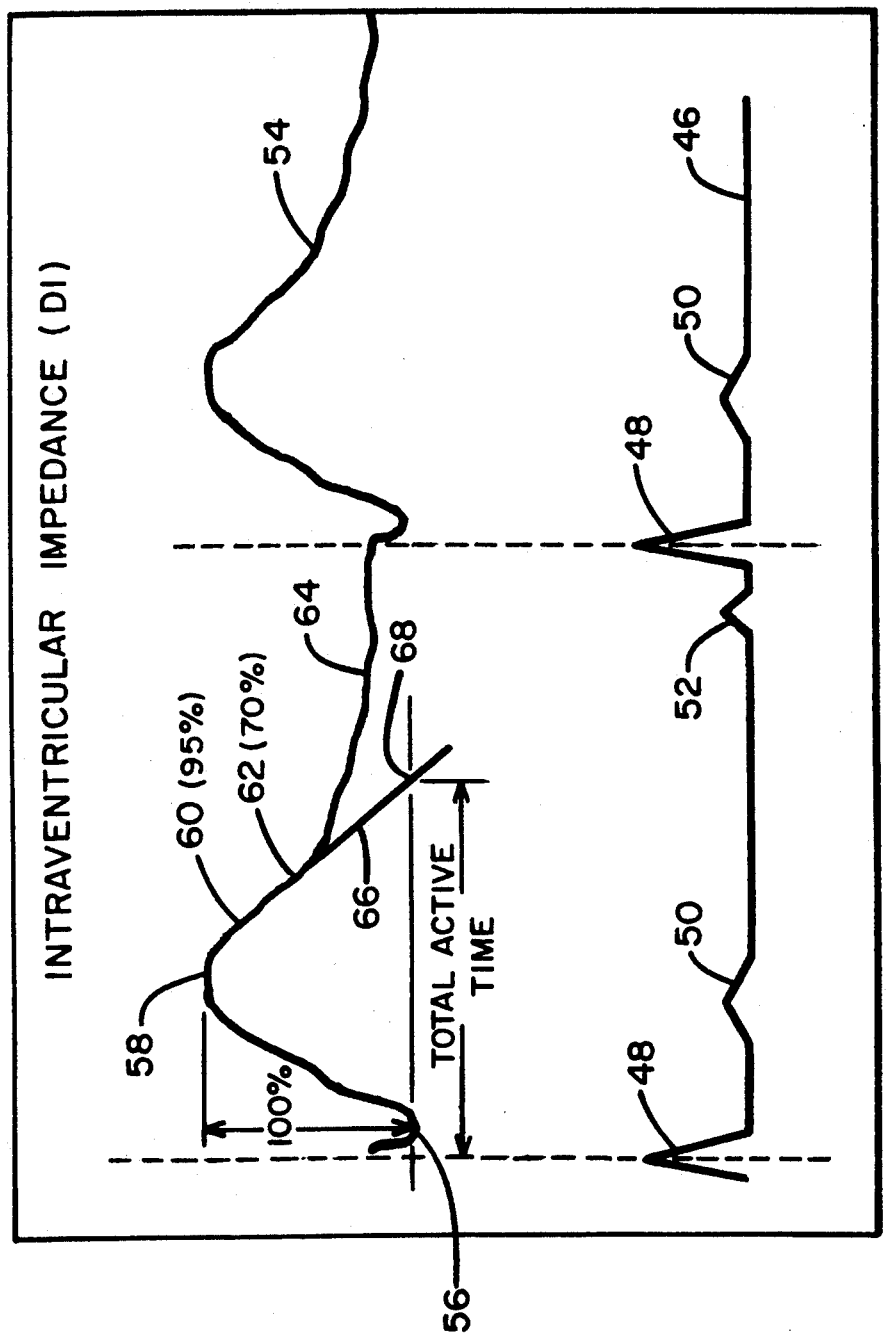
FIG. 4 is a waveform diagram illustrating intracardiac impedance variations with time superimposed with respect to a typical ECG cardiac complex.

Referring first to FIG. 1, there is shown at 10 a representation of a heart in which an endocardial lead 12 has been implanted within the right ventricle thereof. The lead 12 includes a plurality of electrodes including a tip electrode 14, generally disposed in the right apex of the heart and a first sensing electrode 16 disposed proximally of the tip electrode either in the right ventricle, the right atrium, or in the superior vena cava. The lead 12 connects to an implantable cardiac stimulator, such as a pacemaker or a AICD 18 having a metal housing or can 20, at least a portion of which is in ohmic contact with the patient's body tissue. Assuming the device to be a pacemaker, the lead 12 plugs into a connector block 22 formed from an insulating material but including a spot electrode 24 thereon. The pacemaker 18 can thus be said to incorporate a dual indifferent electrode as more particularly described in the Hauck et al. U.S. Pat. No. 5,036,849, assigned to applicant's assignee. The teachings of the Hauck et al. patent are hereby incorporated by reference.

Referring next to FIG. 2, it can be seen that there is contained within the metal can or housing 20 of the device 18, an oscillator 26 which is operatively coupled between the exposed electrode surface 21 of the can 20 and the distal tip electrode 14 on the lead 12. Those skilled in the art will appreciate that there is contained within the lead body 12, elongated, flexible conductors for electrically coupling the electrodes 14 and 16 to the circuitry contained within the can 20. A sense amplifier, filter and demodulator circuit 26 has a first input connected to the spot electrode 24 and a second input connected to the sensing electrode 16 on the lead body 12 When a voltage of a predetermined frequency in the range of from 1 KHz. to 20 KHz. is applied between the tip electrode 14 and the electrode 21 of the can 20, as the heart beats, the alternating current signal from oscillator 26 will be modulated due to the impedance changes resulting from the influx and out-flow of blood from that chamber. That modulated signal is developed between the electrodes 16 and 24 with the amplifier/demodulator/filter circuit 26 being used to create on output line 28 a signal which corresponds to the modulating envelope and is the instantaneous impedance versus time signal. The Z vs. t signal is then applied to an analog-to-digital converter 30 which may, in practice, be an on-board portion of the integrated circuit comprising the microprocessor 32. For ease of representation, however, the A/D converter 30 is shown as a separate component and it operates in a well-known fashion to convert the analog signal Z vs. t on line 28 to a digital representation thereof.

With reference to FIG. 3, it is also envisioned that two leads including atrial lead 33 and ventricular lead 35 may be used, each with a tip electrode 37 and 39 and a ring electrode 41 and 43. By coupling a constant current source 45 across the two tip electrodes 37 and 39 and sensing the signal between the two ring electrodes 41 and 43, a signal proportional to the impedance of the blood volume in these two chambers can be derived and used to compute the heart's Active Time in a manner hereinafter described.

The microprocessor 32 has its data input "D" connected to receive the digital output from the A/D converter 30, via I/O module 33. A system bus 34 contains the necessary data, address and control lines for supporting a ROM memory 36 and a RAM memory 38 and I/O interface module 33.

Stored in the ROM 36 is a program of instructions executable by the microprocessor 32 as well as various fixed constants which may be required. The RAM 38 provides temporary storage for intermediate calculations and the like. The I/O interface 33 allows the bidirectional flow of digital data and commands between the microprocessor and the A/D converter 30 as well as the stimulating pulse generator 42.

The output from the pulse generator 42 is applied through the lead 12 to the tip electrode 14, via a conductor 44, which extends through the lead body 12 from the device 18 to the tip electrode 14. As will be explained in greater detail below, the microprocessor 32 is programmed to compute from the impedance versus time (Z vs. t) signal developed at the output of the amplifier/demodulator/filter circuit 26 the heart's Active Time and then develops a control signal for the pulse generator 42, causing it to emit stimulating pulses at a rate which is proportional to the computed Active Time.

Referring to FIG. 4, numeral 46 refers to a typical ECG wave form showing the QRS complex 48, the T-wave 50, and the P-wave 52. In temporal alignment with the ECG wave form 46 is an impedance versus time wave form 54. This impedance waveform, stored in RAM 38, is approximately the average of the waveforms produced by the previous sixteen beats. To minimize the size of RAM required, an exponential averaging technique is used. To clarify how this average is calculated, an explanation of how one of its points is calculated may be helpful. For instance, consider as an example an impedance point located t ms after the pacing spike or sensed R wave. First, time, t, is set equal to zero at every ventricular pacing spike or sensed ventricular event. The new average impedance ($Z$ avg $_{(n)}$ (t)) valve is then calculated at t ms from the ventricular pacing spike or sensed ventricular event as, $$Z \text{avg}_{(n)}(t\ ms) = \frac{15 \cdot Z \text{avg}_{(n-1)}(t\ ms) + Z_{(n)}(t\ ms)}{16}$$

where n represents the beat number and Z the raw digitized impedance at t ms.

This averaging technique is called ensemble averaging. The ensemble averaged impedance is, in this way, free from any change asynchronous with the heart activity (like respiration, motion, etc.).

It can be seen that the impedance is at a minimum at point 56 just prior to the onset of ventricular contraction. The impedance reaches a maximum at point 58 corresponding to end-systole when the blood volume contained within the heart is at a minimum. At that point, the heart begins to refill and the impedance again begins to decrease, initially at a fast rate, such as between points 60 and 62, and then at a more gentle or slower rate reflected by the decreasing slope of the impedance waveform segment 64.

The time interval labeled Total Active time corresponds to the total time that will elapse from the ventricular pacing pulse or ventricular sensed R-wave (numeral 48 in FIG. 4) to the end of the filling phase, provided that the ventricles are refilled at the fast-filling rate reflected by the slope of the line 66. This parameter value can be estimated by measuring the fast-filling phase rate and calculating the total time needed for the heart to fill to the volume it contained at end-diastole in the previous beat. The end points of the fast-filling phase can be defined, for example, as the end-systolic resistance less 5 percent and less 30 percent of the stroke resistance. These are the points labeled 95 percent and 70 percent, respectively. The microprocessor then computes the time between the ventricular pacing pulse or the ventricular sensed R-wave at point 56 and the intersection between the linear regression line 66 passing through the 95 percent and 70 percent points 60 and 62 and the end-diastolic resistance value associated with the preceding beat, i.e., intersection point 68. This line can also be found using a digital filter (FIR or IIR) to look for the maximum slope during the diastolic portion of the impedance waveform. This slope and the time of the maximum can be used to obtain the least square errors line. Other approaches will be obvious to those skilled in the art.

To maintain hemodynamic stability, pacing must be inhibited during the patient's Active Time. This should be apparent in that if not enough time is provided for the ventricular chambers to fill, assuming the maximum filling rate, cardiac output will necessarily drop. In accordance with the present invention, the heart rate controller, i.e., microprocessor 32 and pulse generator 42, operates to urge the heart rate towards a minimum rate by utilizing the hemodynamic feedback attendant in the use of Active Time as the rate controlling parameter. This can be understood by appreciating that Active Time provides a continuously varying measure of the minimum time needed for the heart to refill. It is responsive to changes in venous return as well as to changes in sympathetic and parasympathetic tone. Active Time causes a rate increment to be added to the existing maximum heart rate on each beat that will maintain hemodynamic stability, i.e., a constant or increasing cardiac output. By preventing pacing rates faster than that maximum, it has been found that AT does not decrease with rate, except during exercise or increased mental stress. Thus, the positive feedback loop tending to drive heart rates higher is disabled.

The equation to calculate the escape rate from the computed Total Active time may be expressed as follows:

$$HR = \frac{60,000}{AT + QG}$$

Where $Q = AT - AT_{min}$. If $Q < 0$ set $Q = 0$. AT is measured in milliseconds and HR in beats per minute.

The parameter G is calculated as:

$$G = \frac{\frac{60,000}{HR_{min}} - AT_{avc}}{AT_{avc} - AT_{min}}$$

where $AT_{avg}$ is the long term average of the Active Time and is used to establish the relationship between the lower rate limit with the average value of AT.

The next beat period (T = 1/HR) is calculated using a 16 beat exponential moving average of the AT calculated using Equation 1 above. If the time interval between the current and next subsequent beat is within plus or minus 20 percent of the current moving average ($T_{avg}$), the moving average is updated. If the new period is outside the range, $T_{avg}$ is changed only 5%. The actual rate will be determined by $HR_{avg} = 1/T_{avg}$. In this fashion, $HR_{avg}$ is constrained to be between the programmable minimum and maximum heart rates established for the microprocessor-based cardiac stimulator.

It is seen then that the maximum hemodynamically stable heart rate (MHSR) is calculated on a beat-by-beat basis as $$MHSR = \frac{60,000}{AT}$$

where AT is measured in milliseconds and used to control the rate at which cardiac stimulating pulses may be produced by the pulse generator 42 of FIGS. 2 or 3. The present invention is the first to use the total Active Time, including electrical depolarization, mechanical contraction, relaxation and fast-filling phase, as the hemodynamic sensor that evaluates the stability of the cardiovascular system.

The Millerhagen et al. application Ser. No. 07/651,318, filed Feb. 5, 1991, and assigned to applicant's assignee, discloses a cardiac stimulating system having a hemodynamically determined upper rate limit. One sensor is employed to adjust the pacing rate as a function of demand while another sensor, determines whether a further rate increase will compromise the heart's hemodynamic performance and, if so, will limit the rate increase accordingly. It should be recognized that the computed total AT can be used as the "governor" for the maximum pacing rate, i.e., to inhibit a further rate increase if to do so would compromise hemodynamic performance.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A cardiac rhythm management device having a variable rate pulse generator and further comprising:
    (a) means for measuring intracardiac impedance variations due to changes in blood volume of the heart;
    (b) means for detecting the occurrence of a natural or stimulated cardiac depolarization signal;
    (c) means for computing from said impedance variations the total active time of a cardiac cycle, said total active time being the interval starting with the occurrence of a detected natural or stimulated cardiac depolarization signal and ending with the completion of the filling phase of the heart with the ventricles assumed to be refilled at their fast filling rate;
    (d) means for producing a control signal related to said total active time; and
    (e) means for applying said control signal to said variable rate pulse generator.

2. In a cardiac rhythm management device of the type including means for sensing cardiac activity including the heart's R-to-R interval and for stimulating cardiac tissue in the event of hemodynamic instability, the improvement comprising:
    (a) means for measuring intracardiac impedance variations due to changes in blood volume in the heart;
    (b) means for computing from said impedance variations the total active time of a cardiac cycle;
    (c) hemodynamic instability determining means for determining whether said R-to-R interval is lower than a predetermined percentage of the computed total active time; and
    (d) means responsive to said hemodynamic instability determining means for activating said means for stimulating cardiac tissue.

3. The device as in claim 2 wherein said means for stimulating cardiac tissue is a defibrillator.

4. In a demand cardiac pacer of the type including a variable rate pulse generator for generating cardiac stimulating pulses in the absence to intrinsic cardiac activity, pacing lead means for coupling said pulse generator to the heart, said pacing lead means having means for sensing said intrinsic cardiac activity and means for applying said stimulating pulses to the heart, the improvement comprising:
    (a) means for measuring the total active time of the cardiac cycle, the total active time being the total time elapsing between the start of a cardiac contraction and the end of the filling phase of the ventricles with the ventricles being filled at their fast filling rate;

(b) means for producing a control signal proportional to said total active time; and (c) means for applying said control signal to said variable rate pulse generator for controlling the rate at which said cardiac stimulating pulses are produced.

5. The demand cardiac pacer as in claim 4 wherein said means for measuring total active time includes means for sensing the intracardiac impedance variations due to the influx and outflow of blood from one ventricular chamber; and means for determining from said intracardiac impedance variations the maximum filling rate following end-systole.

6. The demand cardiac pacer as in claim 4 wherein said means for measuring the total active time includes means for measuring the time interval between one of said cardiac stimulating pulses and said intrinsic cardiac activity and the time where a linear regression of said maximum filling rate reaches the minimum impedance associated with the same beat.

7. In a demand cardiac pacer of the type including a variable rate pulse generator for generating cardiac stimulating pulses at a rate falling between lower and upper rate limits in the absence of intrinsic cardiac activity, pacing lead means for coupling said pulse generator to the heart, said pacing lead means having means for sensing said intrinsic cardiac activity and means for applying said stimulating pulses to the heart and means for sensing a change in physiologic demand coupled to said pulse generator for varying the rate at which said stimulating pulses are produced between said lower and an upper rate limits, the improvement comprising:

(a) first sensing means for sensing the start of a cardiac contraction;

(b) second sensing means for sensing the end of the filling phase of the ventricles with the ventricles being filled at their fast filling rate;

(c) means responsive to said first and second sensing means for measuring the total time elapsing between the start of a cardiac contraction and the end of said filling phase;

(d) means for producing a control signal proportional to said total active time; and (e) means responsive to said control signal for setting said upper rate limit.

8. A cardiac monitor having means for measuring intracardiac impedance changes due to the in-flux and outflow of blood from the heart as its beats, comprising:

(a) first and second electrical leads, each having a distal tip electrode and a surface electrode mounted proximal of said tip electrode, said first lead having its distal tip electrode and its surface electrode adapted for positioning in an atrial chamber of the heart and said second lead having its distal tip electrode and its surface electrode adapted for positioning in a ventricular chamber;

(b) means for coupling a constant current source of a predetermined frequency between only one of said pair of tip electrodes and said pair of surface electrodes;

(c) means for sensing voltage variations across the other one of said pair of tip electrodes and pair of surface electrodes; and (d) microprocessor means coupled to said first and second electrical leads for measuring the impedance between said other of said pair of tip electrodes and pair of surface electrodes; and means including said microprocessor means for computing from said impedance measurements the heart's total active time.

9. A method for controlling an implantable cardiac rhythm management device, comprising the steps of:

(a) measuring the instantaneous intracardiac impedance changes with time due to the influx and outflow of blood from the heart of a patient;

(b) determining from the impedance vs. time measurement the total active time of the cardiac cycle;

(c) producing a control signal proportional to said total active time; and (d) applying said control signal to said cardiac rhythm management device for modifying an operating condition of said device.

10. The method as in claim 9 wherein the step of determining from the impedance vs. time measurement the total active time of the cardiac cycle comprises the steps of:

(a) detecting one of a ventricular sensed R-wave and a ventricular pacing pulse;

(b) determining the volume of blood contained in the heart at end-diastole in a preceding beat;

(c) measuring the fast-filling phase rate from said impedance vs. time measurement; and (d) computing the time interval from a detected one of said ventricular sensed R-wave and a ventricular pacing pulse to the point at which the heart has filled to the volume which it contained at end-diastole in the previous beat.

* * * * *